United States Patent [19]
Rosen et al.

[11] Patent Number: 6,156,540
[45] Date of Patent: Dec. 5, 2000

[54] THROMBIN INHIBITOR

[75] Inventors: Craig A. Rosen, Laytonsville; Liang Cao, Germantown; Mark D. Adams, North Potomac; Rebecca A. Fuldner, Barnesville, all of Md.

[73] Assignee: Human Genome Sciences, Inc., Rockville, Md.

[21] Appl. No.: 08/171,817

[22] Filed: Dec. 22, 1993

[51] Int. Cl.[7] ............................ C12N 15/12; C12N 15/63; C07K 14/47
[52] U.S. Cl. ...................... 435/69.2; 435/172.3; 435/243; 435/320.1; 435/325; 530/350; 536/23.5
[58] Field of Search ................................. 435/69.2, 172.3, 435/240.2, 252.3, 320.1, 325, 243; 530/350; 536/23.5

[56] References Cited

FOREIGN PATENT DOCUMENTS

WO 9102750  3/1991  WIPO .

OTHER PUBLICATIONS

Morgenstein, K. A. et al. *Biochemistry* 33:3432–3441 (1994).

Coughlin, P.B. et al., Identification and Purification of a Novel Serine Proteinase Inhibitor, The Journal of Biological Chemistry, 268 (13):9541–9547 (1993).

Coughlin, P.B. et al., Cloning and Molecular Characterication of a Human Intracellular Serine Protinease Inhibitor, Natl. Acad. Sci. U.S.A., 90:9417–9421 (1993).

*Primary Examiner*—John Ulm
*Assistant Examiner*—Christine Saoud
*Attorney, Agent, or Firm*—Elliot M. Olstein; J. G. Mullins

[57] ABSTRACT

There is provided a thrombin inhibitor polypeptide and DNA(RNA) encoding such polypeptide. Also provided is a procedure for producing such polypeptide by recombinant techniques. The anti-thrombin polypeptide is used to treat various diseases where prevention of blood clotting is necessary and is of therapeutic value. The present invention also discloses a method of producing the anti-thrombin polypeptide and methods for its use as a pharmaceutical composition.

18 Claims, 8 Drawing Sheets

FIG. 1A

```
ATTTGAGGTCCGGGGCTCCGGCGCCTCTGCCCCGCCGTTCTGCTCGCTCCCCGC

TCTGGAGTCTGCCATCATGGATGTTCTCGCAGAAGCAAATGGCACCTTTGCCTTAAACCT
                M  D  V  L  A  E  A  N  G  T  F  A  L  N  L

TTTGAAAACACTGGGTAAAGACAACAACTGAAGAATGTGTTTTTCTCACCCATGAGCATGTC
 L  K  T  L  G  K  D  N  S  K  N  V  F  F  S  P  M  S  M  S

CTGTGCCCCTGGCCATGGTCTACATGGGGGCAAAGGGAAACACCGCTGCACAGATGGCCCA
 C  A  L  A  M  V  Y  M  G  A  K  G  N  T  A  A  Q  M  A  Q

GATACTTTCTTTCAATAAAAAGTGGCGGTGGTGGAGACATCCACCAGGGCTTCCAGTCTCT
 I  L  S  F  N  K  S  G  G  G  G  D  I  H  Q  G  F  Q  S  L

TCTCACCGAAGTGAACAAGACTGGCACGCAGTACTTGCTTAGGATGGCCAACAGGCTCTT
 L  T  E  V  N  K  T  G  T  Q  Y  L  L  R  M  A  N  R  L  F
```

FIG. 1B

```
TGGGGAAAAGTCTTGTGATTCCTCTCATCTTTAGAGATTCCTGCCAAAAATTCTACCA
 G  E  K  S  C  D  F  L  S  S  F  R  D  S  C  Q  K  F  Y  Q

AGCAGAGATGGAGGAGCTTGACTTTATCAGCGCCGTAGAGAAGTCCAGAAACACATAAA
 A  E  M  E  E  L  D  F  I  S  A  V  E  K  S  R  K  H  I  N

CACCTGGGTAGCTGAAAAGACAGAAGGTAAAATTGCGGAGTTGCTCTCCGGGCTCAGT
 T  W  V  A  E  K  T  E  G  K  I  A  E  L  L  S  P  G  S  V

GGATCCATTGACAAGGCTGGTTCTGGTGAATGCTGTCTATTTCAGAGGAAACTGGGATGA
 D  P  L  T  R  L  V  N  A  V  Y  F  R  G  N  W  D  E

ACAGTTTGACAAGGAGAACACCGAGGAGAGACTGTTTAAAGTCAGCAAGAATGAGGAGAA
 Q  F  D  K  E  N  T  E  E  R  L  F  K  V  S  K  N  E  E  K

ACCTGTGCAAATGATGTTTAAGCAATCTACTTTTAAGAAGACCTATATAGGAGAAATATT
 P  V  Q  M  M  F  K  Q  S  T  F  K  K  T  Y  I  G  E  I  F
```

FIG. 1C

```
TACCCAAATCTTGGTGTGCTTCCATATGTTGGCAAGGAACTGAATATGATCATCATGCTTCC
 T  Q  I  L  V  L  P  Y  V  G  K  E  L  N  M  I  I  M  L  P

GGACGAGACCACTGACTTGAGAACGGTGTGGAGAAAGAACTCACTTACGAGAGAAGTTCGTAGA
 D  E  T  T  D  L  R  T  V  E  K  E  L  T  Y  E  K  F  V  E

ATGGACGAGGCTGGACACATGATGGATGAAGAGGAGGTGGAAGTGTCCCCTCCCGGGTTTAA
 W  T  R  L  D  M  M  D  E  E  E  V  E  V  S  L  P  R  F  K

ACTAGAGGAAAGTCTACGACACATGGAGAGTGTCCTGCGCAACCTGGGCATGACTGATGCCTT
 L  E  E  S  Y  D  M  E  S  V  L  R  N  L  G  M  T  D  A  F

CGAGCTGGGCAAGGCAGACTTCTCTGGAATGTCCCAGACAGACCTGTCTCTGTCCAAGGT
 E  L  G  K  A  D  F  S  G  M  S  Q  T  D  L  S  L  S  K  V

CGTGCACAAGTCTTTTGTGGAGGTCAATGAGGAAGGCACGGAGGCTGCAGCCGCCACAGC
 V  H  K  S  F  V  E  V  N  E  E  G  T  E  A  A  A  A  T  A
```

FIG. 1D

```
TGCCATCATGATGATGATGCGGTGTGTGCCAGATTCGTCCCCCGCTTCTGCGCCGACCACCCCTT
 A  I  M  M  M  R  C  A  R  F  V  P  R  F  C  A  D  H  P  F

CCTTTCTTCATCCAGCACAGCAAGACCAACGGGATTCTCTGCGGCCGCTTTTCCTC
 L  F  F  I  Q  H  S  K  T  N  G  I  L  F  C  G  R  F  S  S

TCCGTGAGGACAGGGCAGTCTTGGTGTGCAGCCCCTCCTCTGTCCCCTGACACTCC
 P  *

ACAGTGTGCCTGCAACCCAAGTGGCCTTATCCGTGCAGTGGTGGCAGTTNAGAAATAAAG

GGCCCATTTGTGTGGGATGCCCGCAAAAAAAAAAAAAAAAAAAA
```

1. pD10-TI before IPTG induction
2. pD10-TI after IPTG induction
3. 6 X HI-TI (pD10-TI) after NI-NTA purification
4. Protein markers

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 1366 BASE PAIRS
       (B) TYPE: NUCLEIC ACID
       (C) STRANDEDNESS: SINGLE
       (D) TOPOLOGY: LINEAR (ii) MOLECULE TYPE: cDNA (xi) SEQUENCE DESCRIPTION: SEQ ID NO:1:

```
ATTTGAGGTC CGGGGCGGCT CCGGCGCCTC TGCCCGCCGT TCTGCTCGCT CGCTCCCCGC      60
TCTGGAGTCT GCCATCATGG ATGTTCTCGC AGAAGCAAAT GGCACCTTTG CCTTAAACCT     120
TTTGAAAACA CTGGGTAAAG ACAACTCGAA GAATGTGTTT TTCTCACCCA TGAGCATGTC     180
CTGTGCCCTG GCCATGGTCT ACATGGGGGC AAAGGGAAAC ACCGCTGCAC AGATGGCCCA     240
GATACTTTCT TTCAATAAAA GTGGCGGTGG TGGAGACATC CACCAGGGCT TCCAGTCTCT     300
TCTCACCGAA GTGAACAAGA CTGGCACGCA GTACTTGCTT AGGATGGCCA ACAGGCTCTT     360
TGGGGAAAAG TCTTGTGATT TCCTCTCATC TTTTAGAGAT TCCTGCCAAA AATTCTACCA     420
ABCAGAGATG GAGGAGCTTG ACTTTATCAG CGCCGTAGAG AAGTCCAGAA AACACATAAA     480
CACCTGGGTA GCTGAAAAGA CAGAAGGTAA AATTGCGGAG TTGCTCTCTC CGGGCTCAGT     540
GGATCCATTG ACAAGGCTGG TTCTGGTGAA TGCTGTCTAT TTCAGAGGAA ACTGGGATGA     600
ACAGTTTGAC AAGGAGAACA CCGAGGAGAG ACTGTTTAAA GTCAGCAAGA ATGAGGAGAA     660
ACCTGTGCAA ATGATGTTTA AGCAATCTAC TTTTAAGAAG ACCTATATAG GAGAAATATT     720
TACCCAAATC TTGGTGCTTC CATATGTTGG CAAGGAACTG AATATGATCA TCATGCTTCC     780
GGACGAGACC ACTGACTTGA GAACGGTGGA GAAAGAACTC ACTTACGAGA AGTTCGTAGA     840
ATGGACGAGG CTGGACATGA TGGATGAAGA GGAGGTGGAA GTGTCCCTCC CGCGGTTTAA     900
ACTAGAGGAA AGCTACGACA TGGAGAGTGT CCTGCGCAAC CTGGGCATGA CTGATGCCTT     960
CGAGCTGGGC AAGGCAGACT TCTCTGGAAT GTCCCAGACA GACCTGTCTC TGTCCAAGGT    1020
CGTGCACAAG TCTTTTGTGG AGGTCAATGA GGAAGGCACG GAGGCTGCAG CCGCCACAGC    1080
TGCCATCATG ATGATGCGGT GTGCCAGATT CGTCCCCCGC TTCTGCGCCG ACCACCCCTT    1140
CCTTTTCTTC ATCCAGCACA GCAAGACCAA CGGGATTCTC TTCTGCGGCC GCTTTTCCTC    1200
TCCGTGAGGA CAGGGCAGTC TTGGTGTGCA GCCCCTCTCC TCTCTGTCCC CTGACACTCC    1260
ACAGTGTGCC TGCAACCCAA GTGGCCTTAT CCGTGCAGTG GTGGCAGTTN AGAAATAAAG    1320
GGCCCATTTG TGGGATGCCG CAAAAAAAAA AAAAAAAAA AAAAAA                   1366
```

(2) INFORMATION FOR SEQ ID NO:2:

(i) SEQUENCE CHARACTERISTICS:
       (A) LENGTH: 376 AMINO ACIDS
       (B) TYPE: AMINO ACID
       (C) STRANDEDNESS:
       (D) TOPOLOGY: LINEAR (ii) MOLECULE TYPE: PROTEIN (xi) SEQUENCE DESCRIPTION: SEQ ID NO:2:

Met Asp Val Leu Ala Glu Ala Asn Gly Thr Phe Ala Leu Asn Leu
              5                  10                  15

Leu Lys Thr Leu Gly Lys Asp Asn Ser Lys Asn Val Phe Phe Ser
              20                  25                  30

Pro Met Ser Met Ser Cys Ala Leu Ala Met Val Tyr Met Gly Ala
              35                  40                  45

Lys Gly Asn Thr Ala Ala Gln Met Ala Gln Ile Leu Ser Phe Asn
              50                  55                  60

Lys Ser Gly Gly Gly Asp Ile His Gln Gly Phe Gln Ser Leu
              65                  70                  75

Leu Thr Glu Val Asn Lys Thr Gly Thr Gln Tyr Leu Leu Arg Met
              80                  85                  90

Ala Asn Arg Leu Phe Gly Glu Lys Ser Cys Asp Phe Leu Ser Ser
              95                 100                 105

Phe Arg Asp Ser Cys Gln Lys Phe Tyr Gln Ala Glu Met Glu Glu
             110                 115                 120

Leu Asp Phe Ile Ser Ala Val Glu Lys Ser Arg Lys His Ile Asn
             125                 130                 135

Thr Trp Val Ala Glu Lys Thr Glu Gly Lys Ile Ala Glu Leu Leu
             140                 145                 150

Ser Pro Gly Ser Val Asp Pro Leu Thr Arg Leu Val Leu Val Asn
             155                 160                 165

Ala Val Tyr Phe Arg Gly Asn Trp Asp Glu Gln Phe Asp Lys Glu
             170                 175                 180

Asn Thr Glu Glu Arg Leu Phe Lys Val Ser Lys Asn Glu Glu Lys
             185                 190                 195

Pro Val Gln Met Met Phe Lys Gln Ser Thr Phe Lys Lys Thr Tyr
             200                 205                 210

Ile Gly Glu Ile Phe Thr Gln Ile Leu Val Leu Pro Tyr Val Gly
             215                 220                 225

Lys Glu Leu Asn Met Ile Ile Met Leu Pro Asp Glu Thr Thr Asp
             230                 235                 240

Leu Arg Thr Val Glu Lys Glu Leu Thr Tyr Glu Lys Phe Val Glu
             245                 250                 255

Trp Thr Arg Leu Asp Met Met Asp Glu Glu Val Glu Val Ser
             265                 265                 270

Leu Pro Arg Phe Lys Leu Glu Glu Ser Tyr Asp Met Glu Ser Val
             275                 280                 285

Leu Arg Asn Leu Gly Met Thr Asp Ala Phe Glu Leu Gly Lys Ala
             290                 295                 300

Asp Phe Ser Gly Met Ser Gln Thr Asp Leu Ser Leu Ser Lys Val
             305                 310                 315

Val His Lys Ser Phe Val Glu Val Asn Glu Glu Gly Thr Glu Ala
             320                 325                 330

Ala Ala Ala Thr Ala Ala Ile Met Met Met Arg Cys Ala Arg Phe
             335                 340                 345

Val Pro Arg Phe Cys Ala Asp His Pro Phe Leu Phe Phe Ile Gln
             350                 355                 360

His Ser Lys Thr Asn Gly Ile Leu Phe Cys Gly Arg Phe Ser Ser
             365                 370                 375

Pro (2) INFORMATION FOR SEQ ID NO:3:

```
      (i) SEQUENCE CHARACTERISTICS:
          (A) LENGTH:  30 BASE PAIRS
          (B) TYPE:  NUCLEIC ACID
          (C) STRANDEDNESS:  SINGLE
          (D) TOPOLOGY:  LINEAR (ii) MOLECULE TYPE:  Oligonucleotide (xi) SEQUENCE DESCRIPTION:  SEQ ID NO:3:

CGCAGATCTA TGGATGTTCT CGCAGAAGCA                                              30

(2) INFORMATION FOR SEQ ID NO:4:

(i) SEQUENCE CHARACTERISTICS:
          (A) LENGTH:  60 BASE PAIRS
          (B) TYPE:  NUCLEIC ACID
          (C) STRANDEDNESS:  SINGLE
          (D) TOPOLOGY:  LINEAR (ii) MOLECULE TYPE:  Oligonucleotide (xi) SEQUENCE DESCRIPTION:  SEQ ID NO:4:

CGCTCTAGAT CAAGCGTAGT CTGGGACGTC GTATGGGTAC GGAGAGGAAA AGCGGCCGCA             60
```

THROMBIN INHIBITOR

This invention relates to newly identified polynucleotide sequences, polypeptides encoded by such sequences, the use of such polynucleotides and polypeptides, as well as the production of such polynucleotides and polypeptides. More particularly, the polypeptide of the present invention is a thrombin inhibitor.

The plasmin coagulation system is activated in response to vascular injury. Within a few minutes of the injury, prothrombin is activated through the coagulation cascade to give rise to thrombin. Thrombin then converts fibrinogen to insoluble fibrin, which then interdigitates with and strengthens the primary platelet. Abnormal blood clotting can lead to many vascular diseases, such as stroke, deep vein thrombosis, peripheral arterial occlusion, pulmonary embolism, and myocardial thrombosis which constitute major health risks. Such diseases are caused by either partial or total occlusion of a blood vessel by a blood clot, which contains fibrin and platelets. Two different therapeutics are frequently used for the treatment of thrombosis. One involves the inhibition of thrombin activity, therefore preventing clot formation and the other involves the activation of plasminogen to dissolve the blood clot once it is formed, this is called the fibrinolysis pathway.

Heparin, a compound of the former class, has been widely used to treat conditions, such as venous thromboembolism, in which thrombin activities are responsible for the development or expansion of the thrombus. Although effective, heparin produces many undesirable side effects, including hemorraghing and thrombocytopenia. This has lead to a search for more specific and less toxic anticoagulant.

Hirudin is also a member of the first class and it is a naturally occurring polypeptide which is produced by the blood sucking leach *hirudo medicinalis*. Methods of synthesizing such biologically active molecule which bind to and inhibit thrombin is disclosed in PCT Patent Application No. U.S. 90/04642 applied for by Biogen Inc.

During normal hemostasis, only a very small fraction of thrombin is activated and its protease activity is carefully regulated by protease inhibitors that function as natural anti-coagulants. At least one such protease inhibitor, anti-thrombin III, can in part regulate thrombin activity. It forms complexes with thrombin and other proteases in the coagulation cascade and this interaction is greatly stimulated upon the addition of heparin. It should also be noted that natural mutations in anti-thrombin III are frequently observed and are associated with acute thrombosis.

The fibrinolytic system is activated by deposition of fibrin. When fibrinogen is converted to fibrin, lysine residues become available on the molecule to which plasminogen, the plasma precursor of plasmin, combine tightly. An activator released from endothelial cells (tissue plasminogen activator) activates plasminogen. Activation results from the cleavage of a single peptide bond that converts inert plasminogen into the powerful proteolytic enzyme, plasmin, which degrades fibrin.

Tissue plasminogen activator is thought to be the primary physiologic activator of intravascular fibrin, although endothelial cells release small amounts of a second activator called urokinase. Their activities are regulated by plasminogen activator inhibitor type I and type II.

Very recently, report of purification of a novel serine proteinase inhibitor from human placenta has been disclosed which revealed segments of a polypeptide sequence similar to the polypeptide sequence of the present invention (Coughlin, P B., Tetaz T., and Salem, H H., 1993, the *Journal of Biological Chemistry*, 268, 13, 9541–9547). The results presented in that paper indicate that the polypeptide of the paper could function as a thrombin inhibitor.

In accordance with one aspect of the present invention, there is provided a novel polypeptide which is a thrombin inhibitor, as well as analogs and derivatives thereof. The thrombin inhibitor of the present invention is of human origin.

In accordance with another aspect of the present invention, there is provided a polynucleotide (DNA or RNA) which encodes such polypeptide.

In accordance with still another aspect of the present invention, there is provided a procedure for producing such polypeptide by recombinant DNA techniques.

In accordance with yet a further aspect of the present invention, there is provided the process for utilizing such polypeptide, or DNA sequence encoding for such polypeptide for therapeutic purposes, for example neutralizing thrombin activity.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A, 1B, 1C and 1D, collectively, show the polynucleotide sequence (SEQ ID NO:1) encoding for the thrombin inhibitor, and also show the amino acid sequence (SEQ ID NO:2) of the mature form of the thrombin inhibitor.

Figure 2:
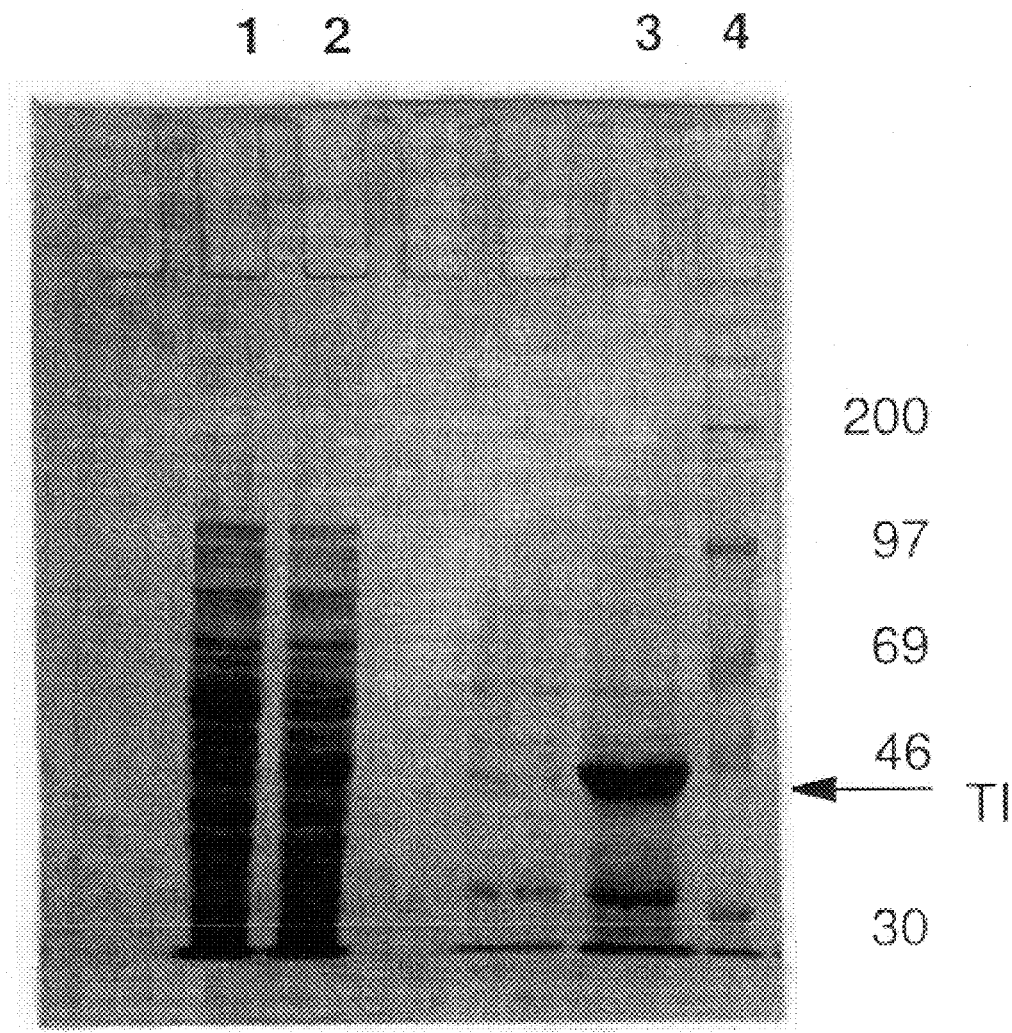
FIG. 2 shows the banding characteristics of the purified thrombin inhibitor polypeptide after bacterial expression, and purification.

In accordance with one aspect of the present invention, there is provided a DNA sequence (and corresponding RNA sequence) as set forth in FIG. 1 of the drawings and/or DNA (RNA) sequences encoding the same polypeptide as the sequence of FIG. 1 of the drawings, as well as fragment portions, derivatives, analogs and all allelic variants of such sequences.

In accordance with another aspect of the present invention, there is provided a polynucleotide which encodes the same polypeptide as the polynucleotide of the cDNA clone deposited as ATCC deposit number 75513, deposited on Aug. 4, 1993, and/or fragments, analogs, derivatives or allelic variants of such polynucleotide.

ATCC Deposit No. 75513, deposited Aug. 4, 1993, is a biological deposit with the ATCC, 12301 Parklawn Drive, Rockville, Md. 20852. Since the strain referred to is being maintained under the terms of the Budapest Treaty, it will be made available to a patent office signatory to the Budapest Treaty.

In the case of DNA, DNA may be single stranded or double stranded, and if single stranded the DNA sequence may be the "sense" strand shown in FIG. 1 or the one complementary thereto.

The polynucleotide (DNA or RNA, preferably DNA) includes at least the portion coding for the polypeptide, which coding portion may be the same as that in the deposited clone or may be different than that in the deposited clone provided that it encodes for the same polypeptide or an allelic variant thereof. The coding portion preferably encodes at least the mature form of the polypeptide of the present invention.

The present invention further relates to polynucleotide sequences which hybridize to the hereinabove-described sequences if there is at least 50% and preferably at least 70% identity between the sequences. In another preferred embodiment the present invention relates to polynucleotide sequences which hybridize under stringent conditions to the hereinabove-described polynucleotide sequences. As herein used, the term "stringent conditions" means hybridization will occur if there is at least 95% and preferably at least 97% identity between the segments. Thus, the present invention includes DNA (RNA) sequences encoding allelic variant forms of the peptide encoded by the DNA of FIG. 1. Thus, the present invention provides isolated DNA (RNA) encoding for a naturally occurring human polypeptide which is a thrombin inhibitor, as well as allelic variants thereof.

The present invention further relates to a polypeptide which is a thrombin inhibitor, and which has the structure shown in FIGS. 1A–1D, as well as allelic variants thereof, and analogs, fragments and derivatives thereof which have the same function as the naturally occurring polypeptide.

The present invention further relates to a polypeptide encoded by the DNA contained in the clone deposited as ATCC number 75513 on Aug. 4, 1993 as well as analogs, fragments, derivatives and allelic variants thereof. These deposits will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with description of sequences herein. A license may be required to make, use or sell the deposited materials, and no such license is hereby granted.

The polypeptide of the present invention is preferably provided in an isolated form, and preferably is purified.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

In a preferred embodiment, the thrombin inhibitor is a full length mature human thrombin inhibitor or an allelic or glycosylated variant thereof. The polynucleotide may also encode a preprotein which is processed and secreted from mammalian cells as the mature protein.

The polynucleotide sequence of the present invention may encode for the mature form of the polypeptide or it may also encode for a leader sequence, which facilitates secretion of the polypeptide. For example, the desired DNA sequence may be fused in the same reading frame to a DNA sequence which aids in secretion of the polypeptide, for example, a leader sequence which functions as a secretory sequence for controlling transport of the polypeptide from the cell of the host. The protein containing a leader sequence is a preprotein and may have the leader sequence cleaved by the host cell to form the mature form of the protein. The polynucleotide of the present invention may also be fused in frame to a marker sequence, for example, a histidine tag which allows for purification of the polypeptide.

Thus, the polypeptide of the present invention may be the mature form of the thrombin inhibitor of the present invention; or may be in the form of a preprotein or prepolypeptide wherein the thrombin inhibitor includes a leader or secretory sequence; or may be in the form of a fusion protein wherein additional amino acids which aid in, for example, purification of the polypeptide are fused to the mature or preprotein at either the 3' or 5' end thereof.

In a preferred embodiment of the present invention, the marker sequence is a hexa-histidine tag added to the coding frame by a bacterial expression vector.

The polypeptide of the present invention is located generally in many organs of the body. However the polypeptide is found predominantly in the testes, lung and heart as shown by the Northern blot analysis of FIG. 4.

As hereinabove indicated, the present invention also includes variants of the polypeptide which is encoded by the DNA of FIGS. 1A–1D or and variants of the DNA contained in the deposited clone, which retains the qualitative activity of such a polypeptide which is a thrombin inhibitor. The variant may be a substitutional variant, or an insertion variant or a deletional variant. Such variants can be naturally occurring allelic variants such as for example, those with different glycosylation patterns or substitution at the amino acid level or deletion at the amino acid level.

Such variants may also be produced by site specific mutagenesis. The substitutional variant may be a substituted conserved amino acid or a substituted non-conserved amino acid, and preferably a conserved amino acid.

The thrombin inhibitor of the present invention is highly expressed in human testes, lung and heart, and less in spleen, prostrate, liver, kidney, gallbladder and ovary. A polynucleotide encoding the polypeptide of the present invention may be obtained from one or more libraries prepared from such tissue.

The polynucleotide of the invention is structurally related to the serine proteinase inhibitor family. It contains an open reading frame encoding a mature protein of 376 amino acid residues, which exhibit significant homology to a number of serine/serpin proteinase inhibitors including plasminogen activator type 1 and type 2, leukocyte elastase inhibitor, and anti-thrombin III precursor.

Host cells are transformed with the expression vectors of this invention and cultured in conventional nutrient media modified as appropriate for inducing promoters, selecting transformants or amplifying the thrombin inhibitor gene. The culture conditions, such as temperature, pH and the like, are those previously used with the host cell selected for expression, and will be apparent to the ordinarily skilled artisan. "Transformation" means introducing DNA into an organism to that the DNA is replicable, either as an extrachromosomal element or by chromosomal integration. Unless indicated otherwise, the method used herein for transformation of the host cells is the method of Graham, F. and dan der Eb, A., Virology 52:456–457 (1973). However, other methods for introducing DNA into cells such as by nuclear injection or by protoplast fusion may also be used. If prokaryotic cells or cells which contain substantial cell wall constructions are used, the preferred method of transfection is calcium treatment using calcium chloride as described by Cohen, F. N. et al., *Proc. Natl. Acad. Sci.* (USA), 69:2110 (1972).

"Transfection" refers to the introduction of DNA into a host cell whether or not any coding sequences are ultimately expressed. Cells do not naturally take up DNA. Thus, a variety of technical "tricks" are utilized to facilitate gene transfer. Numerous methods of transfection are known to the ordinarily skilled artisan, for example, CaPO 4 and electroporation. Transformation of the host cell is the indicia of successful transfection.

The polynucleotide of the present invention may be employed for producing a polypeptide by recombinant techniques. Thus, for example, the polynucleotide sequence may be included in any one of a variety of vectors or plasmids for expressing a polypeptide. Such vectors include chromosomal, nonchromosomal and synthetic DNA sequences, e.g., derivatives of SV40; bacterial plasmids; phage DNA's; yeast plasmids; vectors derived from combinations of plasmids and phage DNAs, viral DNA such as vaccinia, adenovirus, fowl pox virus, and pseudorabies. However, any other plasmid or vector may be used as long as they are replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda PL promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Salmonella typhimurium*; fungal cells, such as yeast, animal cells such as CHO or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE-9 (Qiagen), pBs, phagescript, PsiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, pXT1, pSG (Stratagene) pSVK3, pBPV, pMSG, PSVL (Pharmacia). However, any other plasmid or vector may be used as long as it is replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE, dextran mediated transfection, or electroporation. (Davis, L., Dibner, M., Battey, I., *Basic Methods in Molecular Biology*, (1986)).

The constructs in host cells can be used in a conventional manner to produce the gene product coded by the recombinant sequence. Alternatively, the encoded polypeptide can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., *Molecular Cloning: A Laboratory Manual*, Second Edition, Cold Spring Harbor, N.Y., (1989), the disclosure of which is hereby incorporated by reference.

Transcription of a DNA encoding a polypeptide of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These PBR322 "backbone" sections are combined with an appropriate promoter and the structural sequence to be expressed.

The thrombin inhibitor of the present invention is recovered and purified from recombinant cell cultures by methods including ammonium sulfate precipitation, anion or cation exchange chromatography, phosphocellulose chromatography, hydrophobic interaction chromatography, affinity chromatography (e.g. using DNA or nucleotides on a solid support), hydroxyapatite chromatography and lectin chromatography. It is preferred to have low concentrations (approximately 0.1–5 mM) of calcium ion present during purification (Price et al., *J.Biol.Chem.*, 244:917 (1969)). Following transformation of a suitable host strain and growth of the host strain to an appropriate cell density, the selected promoter is derepressed by appropriate means (e.g., temperature shift or chemical induction) and cells are cultured for an additional period. Cells are typically harvested by centrifugation, disrupted by physical or chemical means, and the resulting crude extract retained for further purification.

Various mammalian cell culture systems can also be employed to express recombinant protein. Examples of mammalian expression systems include the COS-7 lines of monkey kidney fibroblasts, described by Gluzman, *Cell*, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

Recombinant protein produced in bacterial culture is usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

The polypeptide of the present invention may be a naturally purified product, or a product of chemical synthetic procedures, or produced by recombinant techniques from a procaryotic or eukaryotic host (for example, by bacterial, yeast, higher plant, insect and mammalian cells in culture) of a polynucleotide sequence of the present invention. Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue (at position minus 1).

In addition to naturally occurring allelic forms of the polypeptide, the present invention also embraces analogs and fragments thereof, which also function as a thrombin inhibitor. Thus, for example, one or more of the amino acid residues of the polypeptide may be replaced by conserved amino acid residues.

The thrombin inhibitor of the present invention may be used therapeutically or diagnostically to treat or prevent diseases related to thrombosis, which is characterized by hypercoagulation of blood cells. For example, the thrombin inhibitor can be used to prevent proximal extension of deep venous thrombosis or the recurrence of pulmonary embolisms, which are characterized by the lodging of a blood clot in a pulmonary artery with subsequent obstruction of blood supply to the lung parenchyma. The thrombin inhibitor can also be used to prevent the recurrence of cerebral of other systemic embolisms. Further the thrombin inhibitor may be employed to treat high risk patients, such as those who have congestive heart failure, acute myocardial infarction or cardiomyopathy to prevent the development of deep vein thrombosis or pulmonary embolism. The thrombin inhibitor may also be employed as long term therapy for the occasional patient who has recurrent thrombosis or embolism while on the drug warfarin.

The thrombin inhibitor of the present invention, may also be employed in combinations, compositions and methods for treating thrombic disease. For example, the thrombin inhibitor may be combined with a thrombolytic agent (tissue plasminogen activator or urokinase) to work in a complementary fashion to dissolve blood clots, resulting in decreased reperfusion times and increased reocclusion times in patients. The thrombolytic agent dissolves the clot while the thrombin inhibitor prevents thrombin from regenerating the clot. This combination allows the administration of a thrombolytic agent at a considerably lower dosage than if given alone, therefore allowing for the prevention of undesirable side effects associated with the use of a high level of thrombolytic agent, for example, bleeding complications.

The thrombin inhibitor of the present invention may also be used against clot-bound thrombin, which produces clot accretion. This treatment is especially useful since heparin is ineffective against clot-bound thrombin.

Another use of the thrombin inhibitor of the present invention is related to the screening of chemical compounds that either up or down regulate its activity. More specifically, thrombin activity can be assayed with chromogenic substrate Chromozym TH (Boehringer Mannheim Corporation P.O. Box 50414, Indianapolis, Ind. 46250-0414). TH is incubated with thrombin. Its activity is proportional to the linear increase in absorbance at 405 nm. Thrombin inhibitor is incubated with a pool of compound for a fixed length of time before added to thrombin assays to examine the effect of these compounds on thrombin inhibitors. Compounds that specifically affect the thrombin inhibitor can be used to prevent clotting.

The thrombin inhibitor of the present invention may also be used in the treatment of tumor metastases by effectively inhibiting metastatic growth. Fibrin, a product of thrombin proteinase, serves as a substrate for tumor growth, and therefore by inhibiting fibrin deposition through the inhibition of thrombin, the thrombin inhibitor may be used to treat carcinoma of the brain, liver, lung, bone and neoplastic plasma cell carcinoma.

The thrombin inhibitor may also be used in combination and methods for treating neurogenitive diseases. Thrombin is involved in neurite reiteration, a process suggested to change the shape of brain cells and implicated in neurodegenerative diseases, such as Alzheimer's disease and Parkinson's disease.

The action of the thrombin inhibitor of the present invention is independent of heparin (Coughlin, P. B. et al., *Journal of Biological Chemistry*, 268, 13, 9541–9547 (1993)), this is useful since heparin has been noted to cause undesirable side-effects.

The polypeptide of the present invention may also be employed in accordance with the present invention by expression of such polypeptide in vivo, which is referred to as "gene therapy".

Thus, for example, cells from a patient may be transduced with a polynucleotide (DNA or RNA) encoding for the polypeptide in vitro, and the transduced cells are then provided to a patient to be treated with the polypeptide. Such methods are well known in the art. For example, cells may be transduced by procedures known in the art by use of a retroviral particle containing RNA encoding for the polypeptide of the present invention. Similarly, transduction of cells may be accomplished in vivo for expression of the polypeptide in vivo by, for example, procedures known in the art. As known in the art, a producer cell for producing a retroviral particle containing RNA encoding the polypeptide of the present invention may be administered to a patient for transduction in vivo and expression of the polypeptide in vivo.

These and other methods for administering a polypeptide of the present invention by such methods should be apparent to those skilled in the art from the teachings of the present invention. For example, the expression vehicle for transducing cells may be other than a retroviral particle, for example, an adenovirus.

The polypeptide of the present invention may be employed in combination with a suitable pharmaceutical carrier. Such compositions comprise a therapeutically effective amount of the protein, and a pharmaceutically acceptable carrier or excipient. Such a carrier includes but is not limited to saline, buffered saline, dextrose, water, glycerol, ethanol, and combinations thereof. The formulation should suit the mode of administration.

The polypeptide of the present invention may be prepared so as to be administered by injection, by conventional methods using, for example, physiological saline or aqueous solutions containing glucose or other auxiliary agents. The pharmaceutical compositions such as tablets and capsules can also be prepared in accordance with conventional methods. The injections, solutions, tablets and capsules as the pharmaceutical compositions are prepared under aseptic conditions. The amount injected is a therapeutically effective amount, such as from about 1 µg/kg to about 5 mg/kg daily.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptide of the present invention may be employed in conjunction with other therapeutic compounds.

When the thrombin inhibitor of the present invention is used as a pharmaceutical, it can be given to mammals (such as humans, mice, rats, hamster, dogs, rabbits and cats), in a suitable vehicle.

When the polypeptide of the present invention is used as a pharmaceutical as described above, it is given, for example to the above-mentioned subjects in therapeutically effective doses of at least about 10 µg/kg body weight to about 5 mg/kg body weight per day and preferably in doses of from about 5 µg/kg body weight to about 4 mg/kg body weight daily taking into account the routes of administration, symptoms, etc.

Each of the cDNA sequences identified herein or a portion thereof can be used in numerous ways as polynucleotide reagents. The sequences can be used as diagnostic probes for the presence of a specific mRNA in a particular cell type. In addition, these sequences can be used as diagnostic probes suitable for use in genetic linkage analysis (polymorphisms).

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of cDNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clone from which the EST was derived, and the longer the better. For example, 2,000 bp is good, 4,000 is better, and more than 4,000 is probably not necessary to get good results a reasonable percentage of the time. For a review of this technique, see Verma et al., *Human Chromosomes: A Manual of Basic Techniques*, Pergamon Press, New York (1988).

Once a sequence has been mapped to a precise chromosomal location, the physical position of the sequence on the chromosome can be correlated with genetic map data. (Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The protein, its fragments or other derivatives, or analogs thereof, or cells expressing them, can be used as an immunogen to produce antibodies thereto. These antibodies can be, for example, polyclonal, monoclonal, chimeric, single chain, Fab fragments, or the product of an Fab expression library. Various procedures known in the art may be used for the production of polyclonal antibodies.

Antibodies generated against the polypeptide corresponding to a sequence of the present invention can be obtained by direct injection of the polypeptide into an animal or by administering the polypeptide to an animal, preferably a nonhuman. The antibodies so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide. Moreover, a panel of such antibodies, specific to a large number of polypeptides, can be used to identify and differentiate such tissue.

For preparation of monoclonal antibodies, any technique which provides antibodies produced by continuous cell line cultures can be used. Examples include the hybridoma technique (Kohler and Milstein, *Nature*, 256:495–497 (1975)). The trioma technique, the human B-cell hybridoma technique (Kozbor, et al., *Immunology Today*, 4:72 (1983)), and the EBV-hybridoma technique to produce human monoclonal antibodies (Cole, et al., in *Monoclonal Antibodies and Cancer Therapy*, 77–96 (1985)).

Techniques described for the production of single chain antibodies (U.S. Pat. No. 4,946,778) can be adapted to produce single chain antibodies to immunogenic polypeptide products of this invention.

The antibodies can be used in methods relating to the localization and activity of the protein sequences of the invention, e.g., for imaging these proteins, measuring levels thereof in appropriate physiological samples and the like.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., *Nucleic Acids Res.*, 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id, p. 146). Unless otherwise provided, ligation may be accomplished using known buffers and conditions with 10 units to T4 DNA ligase ("ligase") per 0.5 $\mu$g of approximately equimolar amounts of the DNA fragments to be ligated.

EXAMPLE 1

Bacterial Expression and Purification of Thrombin Inhibitor

Figure 5:
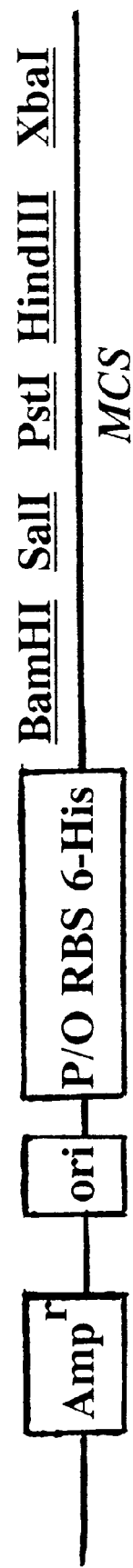
FIG. 5 is a schematic representation of the pQE-9 vector.

Thrombin inhibitor encodes a protein of 376 amino acid residues and is 42.6 Kd in molecular weight. The sequences are shown in FIGS. 1A–1D. The DNA sequence encoding for the full length mature thrombin inhibitor (ATCC #75513) is initially amplified using PCR oligonucleotide primers corresponding to the 5' and 3' end of the DNA sequence to synthesize insertion fragments. The 5' oligonucleotide primer has the sequence (5') CGCAGATCTATGGATGT-TCTCGCAGAAGCA (3')(SEQ ID NO:3), contains a BglI restriction enzyme site followed by 21 nucleotides of thrombin inhibitor coding sequence starting from the initiation codon; the 3' sequence (5') CGCTCTAGATCAAGCG-TAGTCTGGGACGTCGTATGGGTACG-GAGAGGAAAAGCGGCCGCA (3')(SEQ ID NO:4) contains complementary sequences to XbaI site, a translation stop codon, and 21 bp encoding HA tag, the last 21 nucleotides of thrombin inhibitor coding sequence. The restriction enzyme sites correspond to the restriction enzyme sites on the bacterial expression vector pQE-9. (Qiagen Inc., 9259 Eton Avenue, Chatsworth, Calif., 91311). The plasmid vector encodes antibiotic resistance (Amp'), a bacterial origin of replication (ori), an IPTG-regulatable promoter/operator (P/O), a ribosome binding site (RBS), a 6-histidine tag (6-His) and restriction enzyme cloning sites. The pQE-9 vector was digested with BamHl and XbaI and the insertion fragments were then ligated into the pQE-9 vector maintaining the reading frame initiated at the bacterial RBS. (FIG. 5). The ligation mixture was then used to transform the E. coli strain available from Qiagen under the trademark m15/rep4. M15/rep4 contains multiple copies of the plasmid pREP4, which expresses the lacI repressor and also confers kanamycin resistance (Kan'). Transformants are identified by their ability to grow on LB plates containing both Amp and Kan. Clones containing the desired constructs were grown overnight ("O/N") in liquid culture in LB media supplemented with both Amp (100 µg/ml) and Kan (25 µg/ml). The O/N culture is used to inoculate a large culture at a ratio of 1:100 to 1:250. The cells were grown to an optical density of 600 (O.D.600) between 0.4 and 0.6. IPTG ("Isopropyl-B-D-thiogalacto pyranoside") was then added to a final concentration of 2 mM. IPTG induces by inactivating the lacI repressor, clearing the P/O leading to increased gene expression. Cells were grown an extra 3–4 hours. Cells were then harvested by centrifugation. The cell pellet was resuspended in lysis buffer of 10 mM NaPO4. pH 8.0, 140 mM NaCl, 25% sucrose and 1 mg/ml lysozyme. Triton X-100 was added to a final concentration of 1%. The cells were lysed with three time freeze and thaw in dry ice/methanol bath. DNase was added to a final concentration of 150 ug/ml, followed by incubation at 25° C. for 20 minutes and 37° C. for 20 minutes. The cell lysate was centrifuged at micro centrifuge for 10 minutes at top speed. The pellet was washed 5 times with 25% sucrose, 1% triton X-100. The final "white" pellet was then resuspended in 50 mM NaPO4, 1% sarkosyl. Several mg of purified protein can be obtained from a small culture of 50 ml. The final product is more than 90% pure (see FIG. 2).

EXAMPLE 2

Expression of Thrombin Inhibitor in COS Cells

The expression of plasmid, pCDNA1, 4.0 kb was obtain from Invitrogen Corporation. This plasmid contains polyoma virus origin of DNA replication that ensure its replication in culture cell, pCMV promoter that allows high level of expression. The same PCR product was blunted with T4 DNA polymerase and inserted into the EcoRV site of pCDNA 4.0 kb. EcoRV site is downstream of pCMV promoter. Constructs with thrombin inhibitor inserted in the forward or reverse orientation as pCMV promoter were identified and used later for transfection. The HA tag of nine amino acid residues corresponds to an epitope derived from the influenza hemagglutinin protein as previously described (Wilson, I. et al., Cell 37:767 (1984)). The infusion of HA tag at the C-terminals of our target protein allows easy detection of the recombinant protein with a monoclonal antibody that recognizes the HA epitope.

For expression of recombinant thrombin inhibitor, the plasmids containing thrombin inhibitor in either forward and reverse orientation were used to transfect COS cells. $2 \times 10^6$ COS cells were seeded into a 10 cm dish and grown overnight in DMEM media (Gibco BRL, PO Box 68, Grand Island, N.Y. 14072-0068) with 10% fetal calf serum (FCS). Next day, the media was aspirated and the plates were washed with 5 ml of PBS, and transfection cocktails that contain 10 ug DNA per plate, 0.25 mg/ml DEAE dextran in PBS were added to the plates and incubated at 37° C. for 30 minutes with gentle shaking every ten minutes to prevent drying. After 30 minutes, 5 ml of 80 uM chloroquine in serum free DMEM (SF DMEM) was added and further incubated at 37° C. for 2.5 hours. The media were then removed and replaced with 10% DMSO in SF DMEM and let sit for 2.5 minutes. Then the media were removed and the plates were washed once with 5 ml SF DMEM. Finally, 10 ml of DMEM with 10% FCS were added on to these plates and the plates were incubated at 37° C. for two days. After two days, cells were labeled with $^{35}$S methionine for 6 hours in methionine free media. (Ed Harlow and David Lane, Antibodies, Cold Spring Harbor Laboratory Press.)

Figure 3:
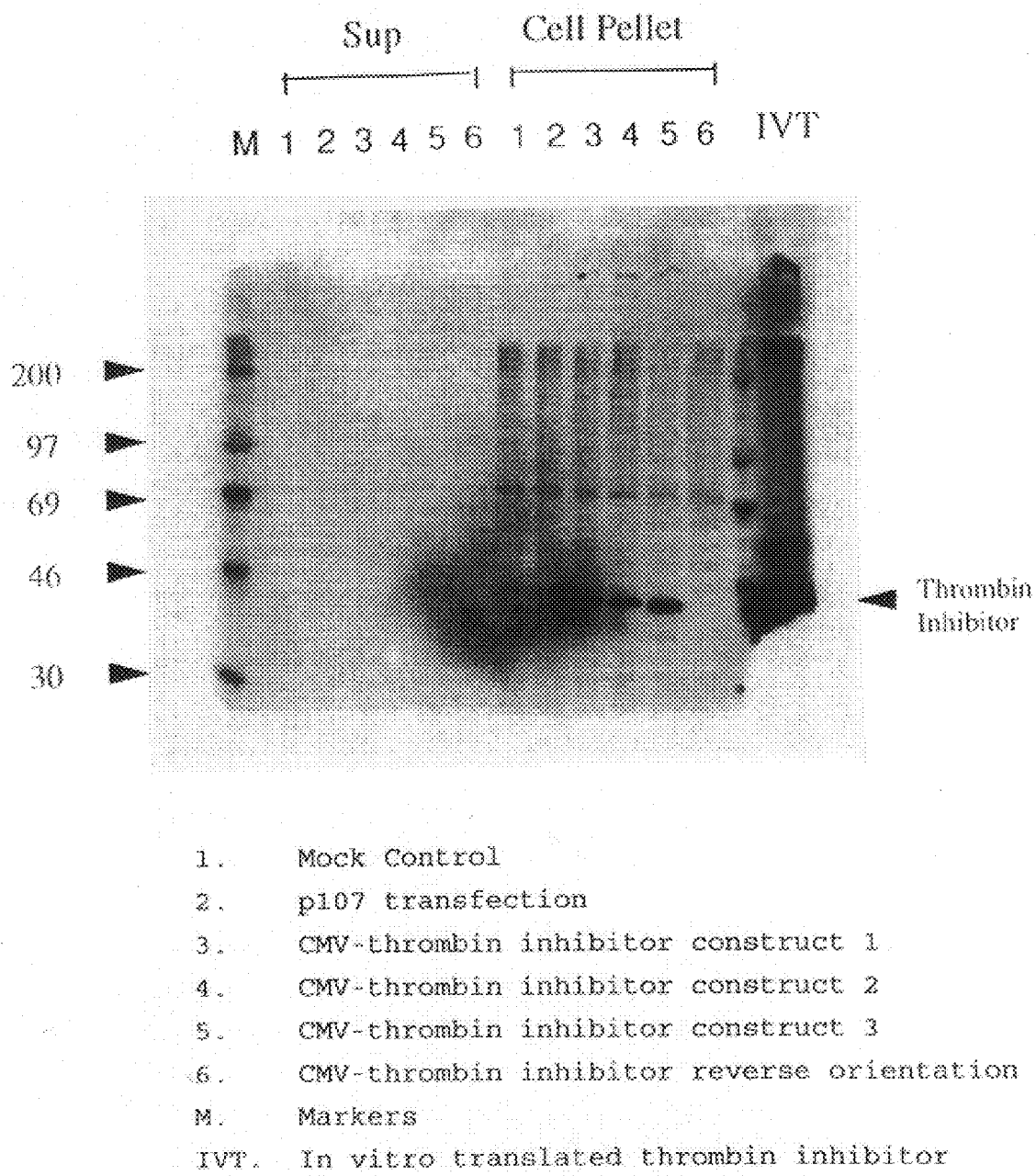
FIG. 3 shows the thrombin inhibitor expressed from CMV promoter in COS cells after immunoprecipitation.

To identify the expression of thrombin inhibitor, immunoprecipitation was carried out under non-denaturing condition to preserve the potential function of the protein. After labeling, the cells were harvested and lysed in lysis buffer of 50 mM This-HCL, pH 7.4, 250 mM NaCl, 0.1% NP 40, 5 mM EDTA at 4° C. and 10% SAC (zysorbin, Zymed Laboratories, Inc., 458 Carlton Court, S. San Francisco, Calif. 94080) was added and the mix was rocked at 4° C. for 30 minutes. After centrifugation for 15 minutes, 0.1 µl of purified HA antibody was added to each tube and incubated for one hour. Protein A beads was added to bring the antibody and bound proteins (Ed Harlow and David Lane, Antibodies, Cold Spring Harbor Laboratory Press). The immuno-precipitates were loaded onto a 10% SDS gel and later steps can be obtained from Ed Harlow and David Lane, Antibodies, Cold Spring Harbor Laboratory Press. The result is shown in FIG. 3.

EXAMPLE 3

Expression Pattern of Thrombin Inhibitor in Human Tissues

Figure 4:
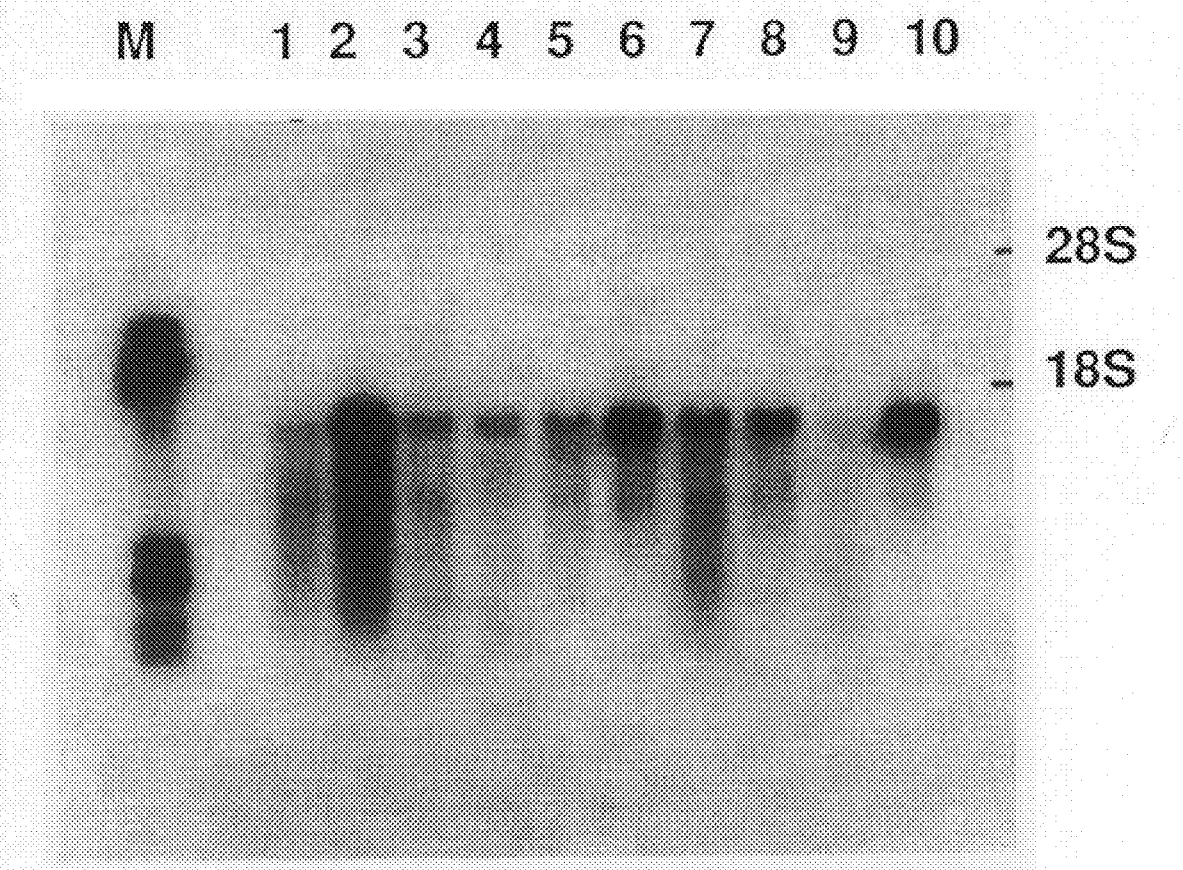
FIG. 4 depicts the results of a Northern blot analysis indicating the organs in which the thrombin inhibitor is predominantly found.

Northern blot analysis was carried out to examine the levels of expression of thrombin inhibitor in human tissues. Total cellular RNA samples were isolated with RNAzol™ B system (Biotecx Laboratories, Inc. 6023 South Loop East, Houston, Tex. 77033). About 10 ug of total RNA isolated from each human tissue specified was separated on 1% agarose gel and blotted onto a nylon filter (Molecular Cloning, Sambrook, Fritsch, and Maniatis, Cold Spring Harbor Press, 1989). The labeling reaction was done according to the Stratagene Prime-It kit with 50 ng DNA fragment. The labeled DNA was purified with a Select-G-50 column from 5 Prime—3 Prime, Inc. 5603 Arapahoe Road, Boulder, Colo. 80303. The filter was then hybridized with radioactive labeled full length thrombin inhibitor gene at 1,000,000 cpm/ml in 0.5 M NaPo$_4$, pH 7.4 and 7% SDS overnight at 65° C. After wash twice at room temperature and twice at 60° C. with 0.5×SSC, 0.1% SDS, the filter was then exposed at −70° C. overnight with an intensifying screen. The message RNA for thrombin inhibitor is abundant in testes, heart and lung, and less so in other tissues. (FIG. 4).

Numerous modifications and variations of the present invention are possible in light of the above teachings and, therefore, within the scope of the appended claims, the invention may be practiced otherwise than as particularly described.

What is claimed is:

1. An isolated polynucleotide comprising a polynucleotide having at least 95% identity to a member selected from the group consisting of:
   (a) a polynucleotide encoding a polypeptide comprising the amino acid sequence from amino acid 2 to amino acid 376 of SEQ ID NO:2; and
   (b) the complement of (a).

2. The isolated polynucleotide of claim 1 wherein said member is (a).

3. The isolated polynucleotide of claim 1 wherein said member is (a) and the polypeptide comprises amino acids 1 to 376 of SEQ ID No:2.

4. The isolated polynucleotide of claim 1 comprising a polynucleotide encoding a polypeptide comprising the amino acid sequence identical to amino acids 2 to 376 of SEQ ID NO:2.

5. The isolated polynucleotide of claim 2, wherein the polynucleotide is DNA.

6. The isolated polynucleotide of claim 1 comprising a polynucleotide encoding a polypeptide comprising the amino sequence identical to amino acids 1 to 376 of SEQ ID NO:2.

7. The isolated polynucleotide of claim 1, wherein said polynucleotide is RNA.

8. A method of making a recombinant vector comprising inserting the isolated polynucleotide of claim 2 into a vector, wherein said polynucleotide is DNA.

9. A recombinant vector comprising the polynucleotide of claim 2, wherein said polynucleotide is DNA.

10. A recombinant host cell comprising the polynucleotide of claim 2, wherein said polynucleotide is DNA.

11. A process for producing a polypeptide comprising:
    expressing from a recombinant cell containing the polynucleotide of claim 4 the polypeptide encoded by said polynucleotide.

12. A process for producing a polypeptide comprising:
    expressing from a recombinant cell containing the polynucleotide of claim 6 the polypeptide encoded by said polynucleotide.

13. The isolated polynucleotide of claim 4 comprising nucleotides 80 to 1204 of SEQ ID NO:1.

14. The isolated polynucleotide of claim 5 comprising nucleotides 77 to 1204 of SEQ ID NO:1.

15. The isolated polynucleotide of claim 5 comprising nucleotides 1 to 1376 of SEQ ID NO:1.

16. An isolated polynucleotide comprising a polynucleotide having at least a 95% identity to a member selected from the group consisting of:
    (a) a polynucleotide encoding the same mature polypeptide encoded by the human cDNA in ATCC Deposit No. 75513; and
    (b) the complement of (a).

17. The isolated polynucleotide of claim 16, wherein the member is (a).

18. The isolated polynucleotide of claim 16, wherein said polynucleotide comprises DNA identical to the coding portion of the human cDNA in ATCC Deposit No. 75513 which encodes a mature polypeptide.

* * * * *